United States Patent [19]

Tam

[11] Patent Number: 5,278,045
[45] Date of Patent: Jan. 11, 1994

[54] METHOD AND COMPOSITIONS TO SCREEN COMPOUNDS FOR ENHANCEMENT OF THE CHOLINERGIC, DOPAMINERGIC AND SEROTONERGIC FUNCTION

[75] Inventor: Sang W. Tam, Hockessin, Del.

[73] Assignee: Du Pont Merck Pharmaceutical Company, Wilmington, Del.

[21] Appl. No.: 486,484

[22] Filed: Feb. 28, 1990

[51] Int. Cl.$^5$ ............................................ G01N 33/53
[52] U.S. Cl. .................................. 435/7.8; 435/7.93; 530/350; 530/388.1; 530/388.22
[58] Field of Search .................. 435/7.9, 7.1, 7.93, 435/7.8; 530/387

[56] References Cited

U.S. PATENT DOCUMENTS

| | | | |
|---|---|---|---|
| 4,760,083 | 7/1988 | Myers et al. | 514/333 |
| 4,857,637 | 8/1989 | Hammonds et al. | 530/403 |
| 4,876,259 | 10/1989 | Myers et al. | 514/256 |
| 4,968,672 | 11/1990 | Jacobson et al. | 514/46 |

FOREIGN PATENT DOCUMENTS 311010 4/1989 European Pat. Off. .

OTHER PUBLICATIONS

Cook, 27th Ann. Mtd. Amer. College of Neuropsychopharmacology, San Juan, Puerto Rico, Dec. 13, 1988.
Saletu et al., Br. J. Clin. Pharmac., vol. 28:1-16 (1989).
Miller et al., Nature, pp. 278-281, vol. 18 (Jan. 18, 1990).
Dixon et al., Nature, pp. 282-284, vol. 18 (Jan. 18, 1990).
Nickolson et al., Drug Development Research, pp. 285-300, vol. 19 (1990).
Cook et al., Drug Development Research, pp. 301-314, vol. 19 (1990).

*Primary Examiner*—Esther L. Kepplinger
*Assistant Examiner*—Donna C. Wortman
*Attorney, Agent, or Firm*—Blair Q. Ferguson; Gildo E. Fato; Lynne Christenbury

[57] ABSTRACT

This invention is directed to a composition comprising a substantially purified protein which enhances endogenous stimulus-induced neurotransmitter release, said neurotransmitter being selected from the group consisting of acetylcholine, dopamine or serotonin, said protein having a binding affinity constant of at least 2.9±0.8 nM for tritiated 3,3-bis(4-pyridinylmethyl)-1-phenylindolin-2-one as determined by a Scatchard analysis, and said protein being trypsin sensitive and phospholipase C insensitive.

3 Claims, 7 Drawing Sheets

METHOD AND COMPOSITIONS TO SCREEN COMPOUNDS FOR ENHANCEMENT OF THE CHOLINERGIC, DOPAMINERGIC AND SEROTONERGIC FUNCTION

FIELD OF THE INVENTION

This invention relates to detection of enhancement of the cholinergic, dopaminergic, and serotonergic function and, in particular, to a screening method and compositions useful in this method to evaluate compounds for enhancing the stimulus-induced release of acetylcholine, dopamine, and serotonin.

BACKGROUND OF THE INVENTION

Recent findings suggest that the cerebral cholinergic system may be involved in the senile decline of cerebral function. Cortical acetylcholine (ACh) synthesis and release decline as a function of age in experimental animals as described by Gibson et al., *J. Neurochem.*, 38, 488 (1982). The primary deficit in patients suffering from Alzheimer's disease is one of cholinergic origin. There is a marked reduction in the number of cholinergic cell bodies in the nucleus basalis of Meynert resulting in a decrease of choline acetyltransferase activity, acetylcholinesterase activity, and acetylcholine synthesis in the cortical and hippocampal projection areas as described by Perry et al., *J. Neuro.*, 40, 503 (1983). Furthermore, the noradrenergic, the dopaminergic, and the serotonergic systems also appear to be deficient in a majority of patients suffering from Alzheimer's disease as described by Davis et al., *Psychopharm. Bulletin*, 19, 451 (1983). Marked deficit in cognitive performance and cortical presynaptic cholinergic markers can be induced by lesioning of the nucleus basalis magnocellularis which contains the cholinergic cell bodies that send their projections to the cortex as described by Lerer et al., *Behav. Neurosci.*, 99, 661 (1985). These cognitive deficits can be attenuated by cholinergic drugs as described by Haroutunian et al., *Life Sci.*, 37, 945 (1985). Moreover, clinical trials with cholinesterase inhibitors like physostigmine and tetrahydroaminoacridine (THA) have shown limited improvement in cognitive measures in Alzheimer's patients: Davis and Mohs, *Am. J. Psychiatry*, 139, 1421 (1982) and Summers et al., *N. Engl. J. Med.*, 314, 1241 (1986).

Researchers have attempted to enhance the neuronal function by using drugs which enhance endogenous stimulus-induced neurotransmitter release which would result in an increase of the amount of neurotransmitter solely when its release is triggered by excitation of the cholinergic neuron. Such action should result in an improvement of the signal-to-noise ratio during transmission in the cholinergic function without the ACh overload toxicity that is typical for cholinesterase inhibitors, or without the distortion of temporal patterns in cholinergic transmission, as caused by direct cholinergic agonists.

Compounds which can be used to enhance the neuronal function are discussed in U.S. Pat. No. 4,760,083, issued to Myers et al. on Jul. 26, 1988, U.S. Pat. No. 4,876,259 issued to Myers et al. on Oct. 24, 1989, and in European Patent Application Publication No. 0311010 which was published on Apr. 12, 1989. 3,3-Disubstituted indolines are described which enhance stimulus-induced release of neurotransmitters, specifically acetylcholine, as well as dopamine and serotonin. These compounds were screened for this activity by evaluating their effect on the release of a neurotransmitter, such as acetylcholine (ACh), from rat cerebral cortex slices using a superfusion procedure described by Mulder et al., *Brain Res.*, 70, 372 (1974) as modified according to Nickolson et al., *Naunyn Schmied. Arch. Pharmacol.*, 319, 48 (1982).

This procedure involves dissecting out an area such as the cortex from rat brain. The brain slices were chopped and incubated with a tritium-labeled neurotransmitter or precursor of the neurotransmitter, e.g., tritiated choline. The brain slices take up the precursor to form the neurotransmitter or they take up the neurotransmitter itself. The labeled drain slices are put into superfusion columns and superfused with a Kreb-Ringers solution. A high potassium Ringers solution is introduced which depolarizes the neurons in the brain slices and induces release of the radiolabeled neurotransmitter (S1). After four minutes, the solution is switched back to the regular Kreb-Ringers solution. A test compound is then introduced into the column and the tissues superfused with the test drug containing solution for twelve minutes after which a second high potassium solution is introduced in the presence of the test compound to stimulate release again (S2). The ratio S2/S1 is compared between the test compounds and the control which is run in the absence of any test drugs. Release enhancers would have a larger S2/S1 ratio compared to that of the control. S1 is used as the internal control for each column. One of the disadvantages of this assay is that it cannot be used to screen large numbers of compounds quickly.

Compounds with such activity can be useful in treating cognitive and/or neurological deficiencies and/or mood or mental disturbances such as found in patients suffering from degenerative nervous system disorders, for example, Alzheimer's disease, Parkinson's disease, senile-dementia, multi-infarct dementia, Huntington's disease, mental retardation, myasthenia gravis, etc.

SUMMARY OF THE INVENTION

This invention is directed to a composition comprising a substantially purified protein which enhances endogenous stimulus-induced neurotransmitter release, said neurotransmitter being selected from the group consisting of acetylcholine, dopamine or serotonin, said protein having a binding affinity constant of at least 2.9±0.8 nM for tritiated 3,3-bis(4-pyridinylmethyl)-1-phenylindolin-2-one as determined by a Scatchard analysis, and said protein being trypsin sensitive and phospholipase C insensitive.

In another embodiment, this invention relates to antibodies or fragments thereof which are capable of binding to this protein or a polypeptide fragment thereof.

Also of concern are screening methods to evaluate compounds for enhancing endogenous stimulus-induced neurotransmitter release, the neurotransmitter being selected from the group consisting of acetylcholine, dopamine, or serotonin.

DETAILED DESCRIPTION OF THE INVENTION

Unless defined otherwise, all technical or scientific terms used herein have the same meaning as commonly understood by one of ordinary skill in the art to which the invention belongs. All publications mentioned herein are incorporated herein by reference.

The term "substantially purified" means synthesized or, if naturally occurring, isolated free of most of the other cellular components with which it is normally associated as illustrated in Example 1.

This invention is directed to a novel, substantially purified protein which enhances endogenous stimulus-induced neurotransmitter release in mammals, said neurotransmitter being selected from the group consisting of acetylcholine, dopamine or serotonin. The protein of this invention can be referred to, in the alternative, as a "DuP 996 binding site" because it binds this compound as discussed below as well as DuP 996 structural analogs. It has been solubilized and isolated free of most of the other cellular components with which it is normally associated using solubilization in nonionic detergent (Table I) and gel filtration chromatography as described below.

Figure 1:
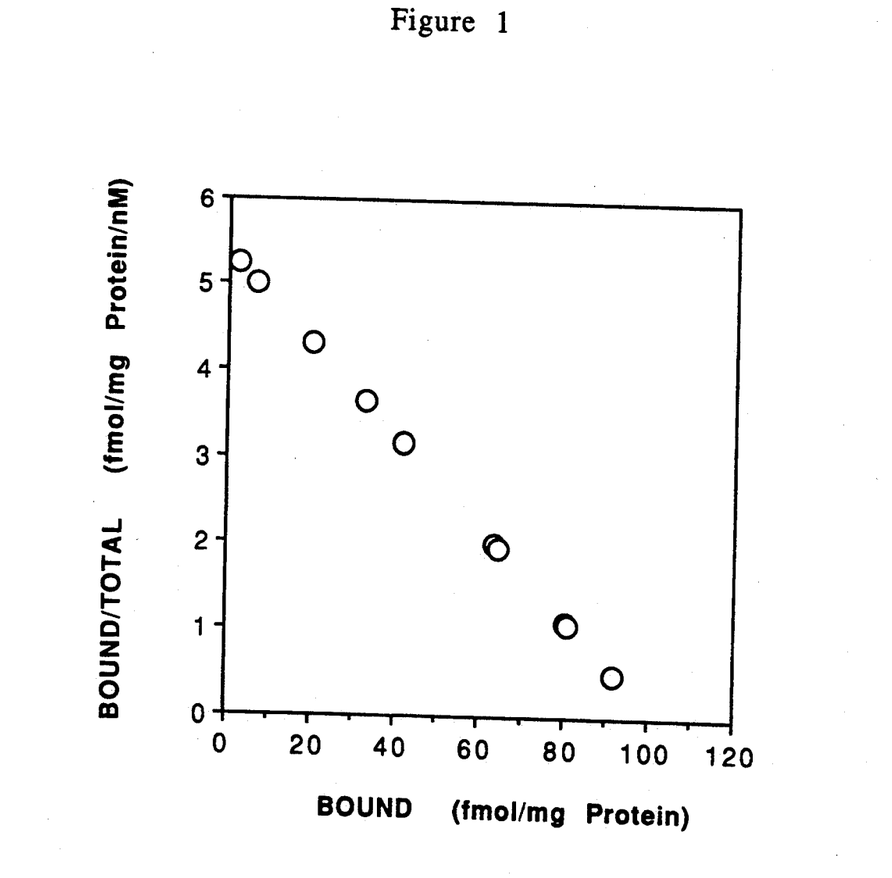
FIG. 1 is a Scatchard plot of the binding of tritiated DuP 996 to the protein of this invention which was obtained from rat brain membranes.

In addition, this novel protein has a binding affinity constant of at least $2.9 \pm 0.8$ nM for tritiated 3,3-bis(4-pyridinylmethyl)-1-phenylindolin-2-one (hereinafter referred to as "DuP 996") as determined by a Scatchard analysis, a procedure well known to those skilled in the art. FIG. 1 is a Scatchard plot of the binding of tritiated DuP 996 to this unique protein which was obtained from rat brain membranes.

Figure 2A:
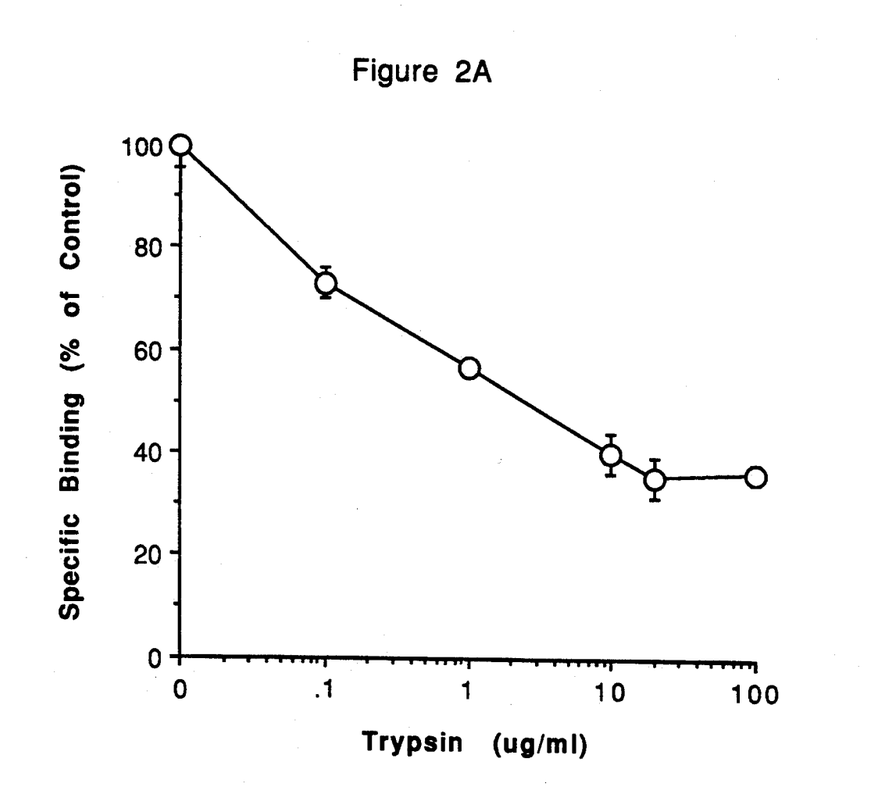
FIG. 2A depicts the loss of tritiated DuP 996 binding activity when the protein in brain membranes was preincubated with different concentrations of trypsin.
Figure 2B:
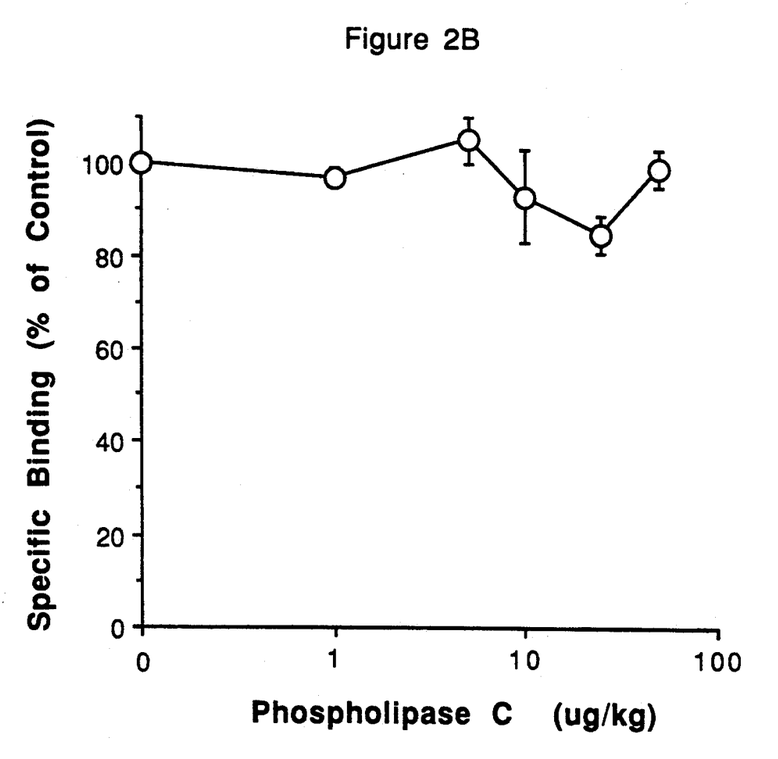
FIG. 2B shows that preincubation with phospholipase C had no effect on the DuP 996 binding activity of the protein of this invention.
Figure 3:
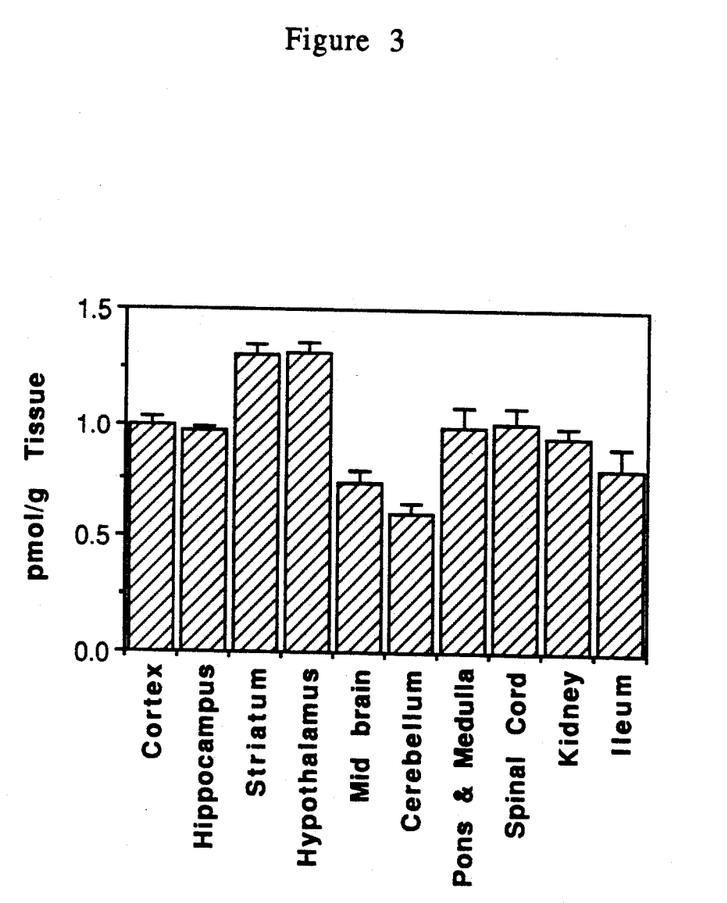
FIG. 3 depicts the regional distribution of tritiated DuP 996 binding sites in rat brain membranes.

As the data presented below show, this protein appears to satisfy the requirement for a unique receptor site. It is sensitive to the protease, trypsin, but not to phospholipase C as depicted in FIG. 2, i.e., it is trypsin sensitive and phospholipase C insensitive. Its binding is specific, saturable, reversible and depends upon concentration, time, pH and temperature. There is regional distribution in the brain as is depicted in FIG. 3.

Figure 4:
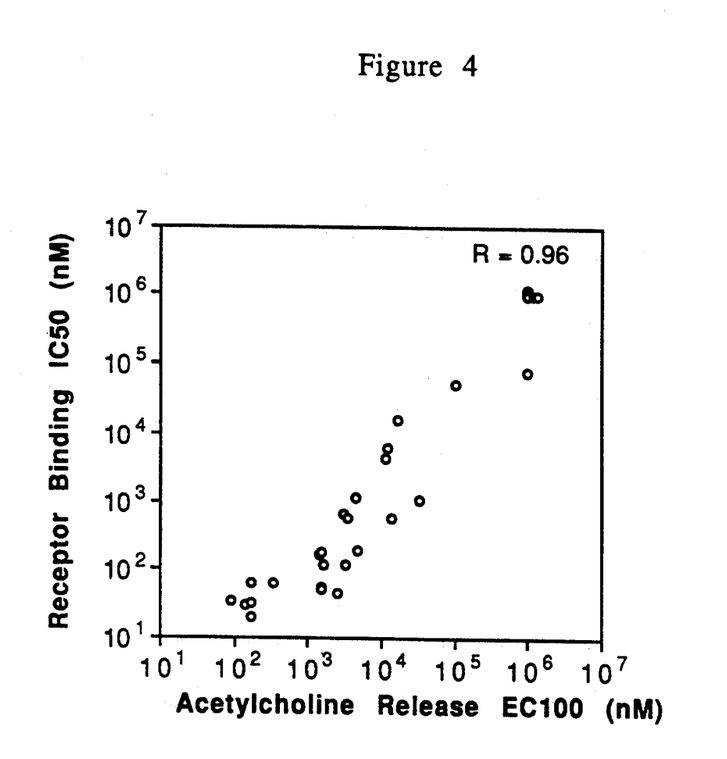
FIG. 4 depicts the correlation of binding affinity of DuP 996 and 29 structural analogs for the tritiated DuP 996 binding site with the concentration of the compounds required to enhance potassium-stimulated ACh release by 100%.

The binding affinity of compounds for this site correlates well with the potency to enhance the release of ACh. This is illustrated in FIG. 4.

Figure 5:
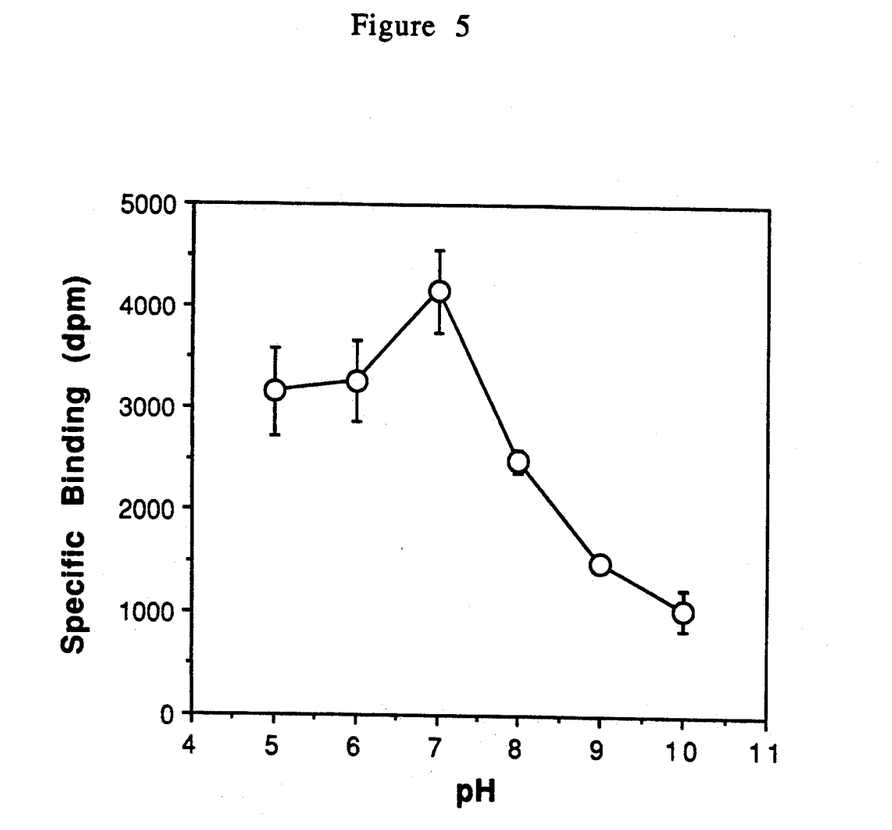
FIG. 5 depicts the pH dependence of the binding of tritiated DuP 996 to the protein of this invention in rat brain membranes.
Figure 6:
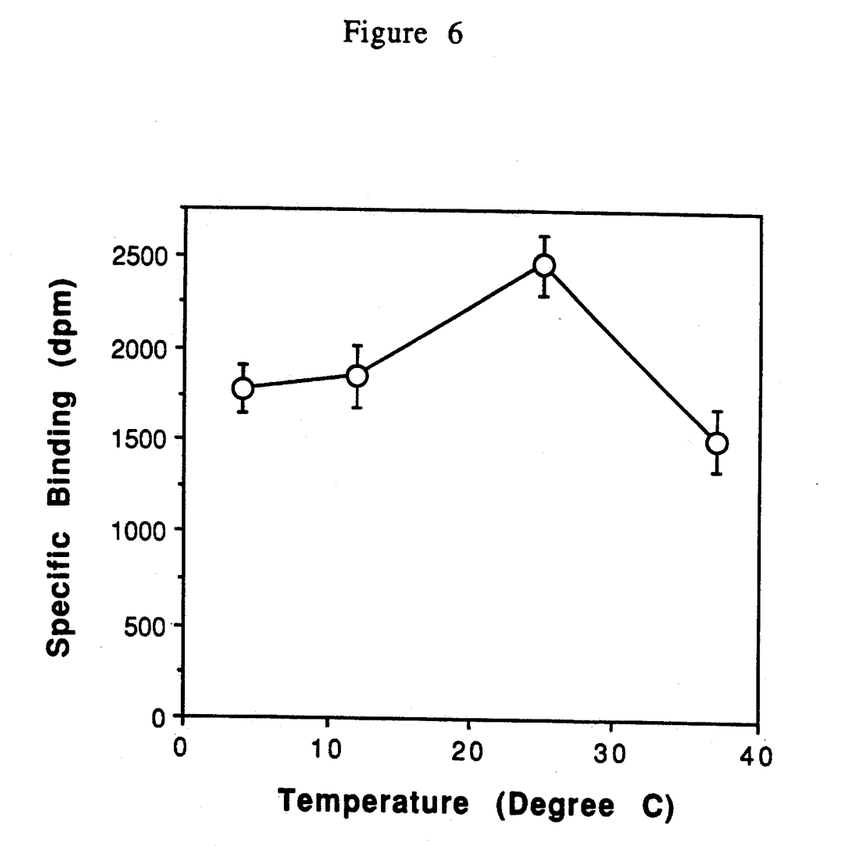
FIG. 6 depicts the temperature dependence of the binding of tritiated DuP 996 to the protein of this invention in rat brain membranes.

FIG. 5 shows that the optimal pH for binding tritiated DuP 996 to the protein of this invention is in the range from pH 6 to pH 8. Preferably, the pH is about 7. In addition, the optimal temperature at which binding occurs is in the range from 12° to 37° C., preferably about 25° C., as is shown in FIG. 6.

This protein was substantially purified by solubilization in nonionic detergent followed by centrifugation to further purify the protein. It retained binding activity for DuP 996 in solubilized form (Table I). CHAPS (3-[(3-cholamidopropyl)-dimethyl-ammonio]-1-propanesulfonate)non-ionic detergent was the preferred detergent in which to solubilize this protein which was further purified by gel filtration chromatography.

Because this protein is ligand selective, as is demonstrated in Example 1, Part C below, and possesses the unique pharmacologic property of enhancing the release of neurotransmitters by neurons, specifically acetylcholine, dopamine, and serotonin, upon depolarization, without affecting baseline release, it can be used to screen large numbers of compounds quickly. As was discussed above, compounds having such activity can be useful in treating cognitive and/or neurological deficiencies and/or mood or mental disturbances such as found in patients suffering from degenerative nervous system disorders, for example, Alzheimer's disease, Parkinson's disease, senile-dementia, multi-infarct dementia, Huntington's disease, mental retardation, myasthenia gravis, etc.

Compounds can be evaluated for their pharmacological usefulness in enhancing the endogenous stimulus-induced release of neurotransmitter such as acetylcholine, dopamine, or serotonin according to the method of this invention by incubating the compounds under investigation with radiolabeled DuP 996 and the protein of this invention and determining the extent to which the compound inhibits the binding of radiolabeled DuP 996 with the protein. This is illustrated further in Example 1, Part G and Example 4, Part B.

Radiolabels which are suitable for practicing the invention include carbon-14, phosphorus-32, Iodide-125, Iodide-131, Technetium-99M, tritium and other radioisotopes commonly used in biological and medical applications. The preferred radiolabel is tritium.

An alternative method according to this invention involves incubating a labeled monoclonal antibody which is capable of binding to the novel protein described herein with the compound under study and the substantially purified protein or a polypeptide fragment thereof and determining the extent to which the compound inhibits the binding of the antibody to the protein.

The term "antibody" as used herein refers to polyclonal antibodies, monoclonal antibodies and/or fragments thereof which are capable of binding to this protein or a polypeptide fragment thereof.

Those skilled in the art will appreciate that the term "antibody" or "immunoreactive" fragment refers to fragments which contain the binding region of the antibody. Such fragments may be Fab-type fragments which are defined as fragments devoid of the Fc portion, e.g., Fab, Fab' and F(ab')$_2$ fragments, or may be so-called "half-molecule" fragments obtained by reductive cleavage of the disulfide bonds connecting the heavy chain components in the intact antibody.

Techniques for making monoclonal antibodies are well known: Kohler and Milstein, *Nature*, 256: 495–497 (1975); Galfre et al., *Methods in Enzymology*, 73:1–46; "Preparation of Monoclonal Antibodies: Strategies and Procedures" (1981); and Kennett et al. (eds.), *Monoclonal Antibodies Hybridomas: A New Dimension in Biological Analyses* (1980).

Monoclonal antibodies are produced by fusing spleen cells for a mouse immunized with the antigen or hapten of interest. For example, the DuP 996 binding protein in isolated brain membranes or in a substantially purified form can be used as the immunogen.

Typically, an animal is immunized with the immunogen of interest, emulsified in an adjuvant, and boosted at regular intervals. The serum is assayed for the presence of the desired antibody by any convenient method, frequently an enzyme-linked immunosorbent assay (ELISA), a radioimmunoassay (RIA) or a radioreceptor assay. When an acceptable titer or antibody is detectable in the serum, the animal is sacrificed and the spleen is removed aseptically for fusion.

Several different murine (mouse) myeloma cell lines deficient in hypoxanthine guanine phosphoribosyl transferase (HGPRT) are known to be suitable as fusion partners. The features of some of these cell lines are described in Current Topics in Microbiology and Immunology, 81, F. Melchers, M. Potter, and N. Warner, ed., Springer-Verlag, 1978.

Fusion is carried out most commonly by using polyethylene glycol as a fusion promoter. After fusion, the cells are diluted and cultured in a selective medium containing hypoxanthine, aminopterin and thymidine (HAT). Cells can be supplemented with insulin to enhance the formation and growth of hybridomas. When sufficient cell growth has occurred, the culture supernatant is sampled and tested by any convenient means, frequently ELISA, radioreceptor assay or RIA. Those cultures which contain antibody of interest are then cloned by limiting dilution, retested and expanded.

Large volumes of antibody can then be obtained by growing the hybridoma in vitro and harvesting the culture supernatant. Antibodies can also be harvested from the ascites fluid of syngeneic mice which have been injected intraperitoneally with the hybridoma cells.

The antibody is purified using techniques well-known in the art. Chromatography on staphylococcal protein A is one such method. The monoclonal antibody thus generated can be characterized by its immunoglobulin class and subclass.

In accordance with this invention, monoclonal antibodies can be labeled using conventional techniques. The method selected will depend to some extent upon the type of linkage desired and the tolerance of the antibody to various conjugation chemistries.

Two commonly used radioisotopes are $^{125}I$ and $^3H$. Standard radioactive isotopic labeling procedures include the chloramine T, lactoperoxidase and Bolton-Hunter methods for $^{125}I$ and reductive methylation for $^3H$.

Enzymes which can be used as labels include, but are not limited to, horseradish peroxidase, alkaline phosphatase, betagalactosidase, glucose oxidase, luciferase, beta-lactamase, urease, and lysozyme. Labeling with enzymes is facilitated by using dialdehyde, carbodiimide coupling, homobifunctional crosslinkers and heterobifunctional crosslinkers. The labeling method chosen depends on the functional groups available on the enzyme and the material to be labeled, and the tolerance of both to the conjugation conditions. The labeling method used in accordance with the present invention can be any one of the conventional methods available such as those described by Engvall and Pearlmann, Immunochemistry, 8, 871 (1971), Avrameas and Ternynck, Immunochemistry, 8, 1175 (1971), Ishikawa et al., J. Immunoassay 4(3): 209-327 (1983) and Jablonski, Anal. Biochem. 148: 199 (1985).

Other labeling methods include the use of fluorogenic, chemiluminescent or electrochemical labels.

The invention can be further understood by the following examples:

EXAMPLE 1

Part A: Preparation of Brian Membranes

Male Sprague-Dawley rats (Charles River Breeding Laboratories) at 200-250 g were euthanatized by decapitation. Rat brain regions were dissected according to Heffner et al., Pharmacol. Biochem. Behav., 13, 453 (1980). Brain membranes were prepared by the method of Tam, Proc. Natl. Acad. Sci. USA, 80, 6703 (1983). The brain tissues were homogenized (20 sec) in 10 vol (wt/vol) of ice-cold 0.32M sucrose with a Brinkman Polytron (setting 8). The homogenate was centrifuged at 920×g for 10 min at 4° C. The supernatant was centrifuged at 47,000×g for 20 min. The resulting membrane pellet was resuspended in 10 vol (original wt/vol) of 50 mM Tris-HCl (pH 7.4) and incubated at 37° C. for 30 min to degrade and dissociate bound endogenous ligands. The membranes were then centrifuged at 47,000×g for 20 min and resuspended in 50 mM Tris-HCl.

Part B: Receptor Binding

Membranes (1-2 mg of protein) were incubated with various concentrations of tritiated DuP 996 (41.5 Ci/mmol) in 50 mM Tris-HCl buffer, pH 7.4 in a final volume of 1 ml in room temperature for 60 minutes. The samples were rapidly filtered by Whatman GF/B glass filters under negative pressure and washed 3 times each with 5 ml of ice-cold Tris buffer. The filters were presoaked for 3 hr in 0.2% polyethylenimine and washed twice before sample filtration. Bound radioactivity (dpm=disintegration per minute) was determined by liquid scintillation counting. Nonspecific binding was determined in the presence of 10 micromolar DuP 996. A concentration of 10 nanomolar DuP 996 was used in displacement studies. The binding constant Kd was determined by Scatchard analysis using LIGAND computer curve fitting program of Munson and Rodbard, Anal. Biochem., 107, 220 (1980) and a kd of 2.9±0.8 nM was determined for tritiated DuP 996. This is set forth in FIG. 1. The insert in FIG. 1 shows the data for the saturation binding experiment with the amount of total, nonspecific, and specific binding of [$^3H$]DuP 996.

Part C: Specificity of the DuP 996 Binding Protein 37 pharmacological standards which include receptor and ion channel ligands and neuropentides were tested in the tritiated DuP 996 receptor binding assay to determine the specificity and selectivity of the DuP 996 binding protein, the pharmacological standards tested were ACTH 1-24, adenosine, 3,4-aminopyridine, amitriptyline, amphetamine, angiotensin III, atropine, bradykinin, caffeine, cimetidine, cholecystokinin, diazepam, diltiazem, GABA, haloperidol, isoproterenol, LHRH, mianserin, naloxone, neurokinin A, neurokinin B, neurotensin 8-13, nicotine, norepinephrine, N-methyl-D-aspartic acid, piracetam, phencyclidine, pentylenetetrazol, pyrilamine, (+)-SKF 10,047, strychnine, substance P, tetrahydroaminoacridine, thyrotropin, verapamil, veratidine, and yohimbine. None of these pharmacological standards was able to displace tritiated DuP 996 binding from the binding protein.

Part D: Solubilization of Binding Protein

The nonionic detergent CHAPS at 20 mM in 50 mM Tris-HCl buffer, pH 7.4, with bacitracin (50 μg/ml) was added to brain membranes at a ratio of 3.15 ml to membranes prepared from 1 rat brain and mixed extensively. The mixture was centrifuged at 47,000×g for 20 minutes. The supernatant containing the solubilized protein was collected. The supernatant from centrifugation of brain membranes without detergent was used as the control.

Part E: Binding to Solubilized Protein

Fifty µl aliquots of the solubilized membrane protein were incubated with 0.2 ml of 50 mM Tris-HCl, pH 7.4, with 0.1% bovine serum albumin, and 10 nM tritiated DuP 996 in a total volume of 0.325 ml. Nonspecific binding was determined in the presence of 10 µM DuP 996. After 1 hour of incubation at 25° C., 0.5 ml of ice-cold 0.1M sodium phosphate buffer, pH 7.4, with 0.1% bovine gamma globulin was added. The sample was put on ice and then 0.5 ml of 25% (w/v) polyethylene glycol 8000 was added and mixed. The sample was put on ice for 10 to 15 minutes and filtered through Whatman GF/B filters which had been presoaked in 0.2% polyethylenimine. The filtered sample was washed twice with 3 ml each of ice cold 8% polyethylene glycol 8000 in 100 mM Tris-HCl, pH 7.4. Bound radioactivity retained on the filters was counted in a liquid scintillation counter.

TABLE I

Specific [$^3$H]DuP 996 Binding to
Detergent Solubilized Rat Brain Membrane Proteins

| DETERGENT | SPECIFIC BINDING (dpm) |
|---|---|
| Control | 7 |
| CHAPS, 20 mM | 868 |
| Octyl glucoside, 0.4% | 511 |
| NP40 | 348 |
| Tween 80, 1% | 134 |
| Triton X-100, 1% | 0 |

Part F: Purification by Gel Filtration Chromatography

The binding protein was purified by gel filtration molecular sieve chromatography. A 2.6 cm × 100 cm glass column was packed with Sephacryl S-300 superfine gels with a separation range of 10–1500 kilo daltons. The column was equilibrated with 8 mM CHAPS detergent, 0.3M NaCl in 50 mM Tris-HCl buffer, pH 7.4 (column buffer). Brain membranes, prepared from a rat brain, were solubilized in 3.15 ml 20 mM CHAPS in 50 mM Tris-HCl buffer, pH 7.4, with bacitracin (50 µg/ml), and centrifuged at 47,000 × g for 20 min. The supernatant was collected and incubated with 10 nM tritiated DuP 996 in column buffer for 60 min at 25° C. and then loaded onto the column. The samples were eluted with the column buffer at a flow rate of 150 ml/hr. Fractions of 3 ml per tube are collected. To determine nonspecific binding, similar experiments were performed in the presence of 10 nM DuP 996 during the incubation with tritiated DuP 996. Blue dextran was used to determine the void volume. 0.5 ml aliquots of the fractions were counted in a liquid scintillation counter to determine the radioactivity of tritiated DuP 996 bound to the solubilized protein.

Part G: Radioreceptor Screening Assay

Compounds to be screened were incubated with brain membranes, (1–2 mg protein) in 50 mM Tris-HCl buffer, pH 7.4, for 10 minutes in 25° C. Then 10 nM tritiated DuP 996 or its active structural analogs were added and incubated at 25° C. for 60 minutes. The samples were filtered on Whatman GF/B glass filters which had been soaked in 0.2% polyethylenimine and washed 3 times each with 5 ml of ice-cold Tris buffer. Nonspecific binding was determined by performing binding in the presence of 10 µM DuP 996. The control represents specific binding in the absence of compounds to be screened. Screened compounds which inhibited the specific binding of tritiated DuP 996 or analogs to its binding protein should be active in binding to the same protein. This is illustrated further in Example 4, Part B.

EXAMPLE 2

Part A: Trypsin Pretreatment

One ml aliquots of brain membranes (1–2 mg of protein) in 50 mM Tris-HCl buffer, pH 7.4, were incubated with 0.1–100 µg/ml of trypsin (17,000 BAEE units/mg protein) at 25° C. for 10 min. 10 nM of tritiated DuP 996 was added and incubated for 45 min at 25° C. for ten minutes. Samples were filtered on Whatman GF/B filters which had been presoaked in 0.2% polyethylenimine under negative pressure and washed 3 times with ice-cold buffer. Nonspecific binding was determined in the presence of 10 µM DuP 996.

Part B: Phospholipase C Pretreatment

One ml aliquots of brain membranes (1–2 mg of protein) in 50 mM Tris-HCl buffer, pH 7.4, were incubated with 5–50 µg/ml of phospholipase C for 10 min at 37° C. 10 nM of tritiated DuP 996 was added and incubated for 45 min at 25° C. Samples were filtered on Whatman GF/B filters which had been presoaked in 0.2% polyethylenimine under negative pressure and washed 3 times with ice-cold buffer. Nonspecific binding was determined in the presence of 10 µM DuP 996.

EXAMPLE 3

Part A: Regional Distribution

Rat brain regions were dissected according to the method of Heffner et al., Pharmacol. Biochem. Behav., 13, 453 (1980). Membranes from different brain regions were prepared according to the method described in Example 1, Part A. To determine binding, membranes were incubated with 10 µM tritiated DuP 996 according to the method described in Example 1, Part B. Regional distribution is depicted in FIG. 3.

EXAMPLE 4

Part A: Neurotransmitter Release Assay

Male Wistar rats weighing 175–200 g were euthanatized and the brains were dissected out immediately. Slices (0.3 mm thick) from the parietal cortex were prepared manually by using a recessed Lucite ® guide. Slices (1.5 mm thick) from the hippocampus and the caudate nucleus were prepared by using a slotted brain holder. All slices were subsequently cut into 0.25 × 0.25 mm squares with a McIlwain tissue chopper.

Labeling of transmitter stores in slices was prepared by the following methods. For ACh release, slices (approximately 100 mg wet weight) were incubated in 10 ml Krebs-Ringer (KR) medium containing (mM): NaCl(116), KCl(3), $CaCl_2$(1.3), $MgCl_2$(1.2), $KH_2PO_4$(1.2), $Na_2SO_4$(1.2), $NaHCO_3$(25) and glucose(11), to which 10 µCi $^3$H-choline (specific activity approx. 80 Ci/mmol: NEN) and 10 nmol unlabeled choline had been added to give a final concentration of $10^{-6}$M. Incubation was carried out for 30 min at 37° C. under a steady flow of 95% $O_2$/5% $CO_2$. Under these conditions, part of the radioactive choline taken up is converted into radioactive ACh by cholinergic nerve endings, stored in synaptic vesicles, and released upon depolarization by high-$K^+$-containing medium [Molenaar et al., 1973a]. For dopamine (DA), serotonin (5-HT), and norepinephrine (NE) release, slices (approximately 100 mg wet weight) were incubated in KR medium containing 0.01 mM nialamide at 37° C. under a steady flow of 95% $O_2$/5% $CO_2$. The MAO-inhibitor nialamide was added to the medium in order to inhibit metabolism to the monoamines. Incubation was for 30 min in 10 ml of KR medium to which 10 μCi $^3$H-dopamine, $^3$H-norepinephrine, or $^3$H-5-hydroxytryptamine (specific activity 30, 45, and 78 Ci/mmol, respectively: all from NEN) had been added.

Separate experiments were performed for the release of each neurotransmitter. After labeling of the transmitter stores, the slices were washed three times with non-radioactive KR medium and transferred to a superfusion apparatus to measure the drug effects on transmitter release [Schoemaker et al., *Psychopharmacology* 74, 137 (1981)]. The superfusion apparatus consisted of 10 thermo-jacketed glass columns of 5 mm diameter which were provided with GF/F glass fiber filters to support the brain slices (approximately 10 mg tissue/column). Superfusion was carried out with KR medium at a rate of 0.3 ml/min. For ACh release, $10^{-5}$M hemicholinium-3 was added to the medium to prevent the uptake of choline formed during superfusion from phospholipids and released ACh, so that it could not be subsequently converted into newly synthesized ACh, which would be released in preference to the pre-formed, labeled ACh. The medium was delivered by a 25-channel peristaltic pump (Ismatec; Brinkman) and maintained at 37° C. by a thermostated stainless-steel heating coil before entering the superfusion column. Each column was provided with a four-way slider valve (Beckman Instruments) which allowed rapid change of low-to-high-$K^+$-KR-medium and with two 10-channel, 3-way valves which were used to change form drug-free to drug-containing low- and high-$K^+$-KR media.

After 15 min washout of non-specifically bound radioactivity during superfusion, the collection of fractions of 4 min (1.2 ml) each was started. After 3×4 min, the KR medium was changed to a KR medium with 25 mM KCl (ACh, 5-HT release) or 12.5 mM KCl (DA release) (high $K^+$-KR medium; S1). Depolarization-induced stimulation of release by high-$K^+$-KR medium was then substituted by drug- or vehicle-containing low- and high-$K^+$-KR medium and superfusion continued for 3×4 min with low-$K^+$-KR medium, for 1×4 min with high-$K^+$-KR medium (S2), and for 2×4 min with low-$K^+$-KR medium.

Compounds were added to the medium by 100-fold dilution of appropriate stock solutions (in 0.9% NaCl/$H_2O$) with either low- or high-$K^+$-KR medium.

All superfusion fractions were collected in liquid scintillation counting vials. After superfusion, the slices were removed from the superfusion columns and extracted in 1.0 ml of 0.1N HCl. To each superfusion fractions and extracts, 12 ml Liquiscint ™ scintillation cocktail was then added and samples were counted in a Packard Tricarb Liquid Scintillation Counter. No corrections were made for quenching.

The rate of release was expressed as fractional rate constant (frc) which is equal to the dpm of the fraction divided by the total dpm in the slices at the beginning of the fraction × the time of fraction. For each column the increase in frc during stimulation (frc$_{S2}$) measured in the presence of vehicle or drug was divided by the corresponding frc$S_1$ to yield the S2/S1 ratio. Drug effects were evaluated by expressing this ratio for experimental columns (drug present during S2) as a percentage of the ratio calculated for the concomitantly run control columns (no drug present during S2).

Students t-test was used to analyze the results statistically.

Part B: Correlation of Receptor Binding Affinity with ACh Release Enhancing Activity DuP 996 receptor binding affinities (Ki) for DuP 996 and 29 structural analogs (Table II) were determined by displacement binding studies using the method described in Example 1, Part G. The binding affinities were expressed as IC$_{50}$s which represent the effective concentration of the compounds needed to inhibit binding of tritiated DuP 996 by 50 percent.

The effective concentration of compounds required to enhance stimulated release of ACh by 100% (2-fold) over that of the control (EC$_{100}$) was calculated from the dose response curves of the compounds.

The DuP 996 receptor affinities of the test compounds correlate very well with the potency of these compounds to enhance stimulated release of ACh. The data presented in FIG. 4 indicate that the DuP 996 binding protein is a functional receptor with activity in enhancing neurotransmitter release.

TABLE II

| Compounds | Binding IC$_{50}$ (nM) | ACh Release EC$_{100}$ (nM) |
| --- | --- | --- |
| 1. 1-[9,9-Bis(4-pyridinylmethyl)-9H-fluoren-2-yl]-ethanone | 20 | 170 |
| 2. 9,9-Bis(4-pyridinylmethyl)-9H-fluorene-2-amine | 30 | 140 |
| 3. 10,10-Bis-(4-pyridinylmethyl)-1,8-dichloro-9(10H)-anthracenone | 32 | 170 |
| 4. 10,10-Bis(4-pyridinylmethyl)-9(10H)-anthracenone | 34 | 90 |
| 5. 2,2-Bis(4-pyridinylmethyl)-6,7-dihydro-indole(1,7-AB)(1)-benzapin-1(2H)-one | 46 | 2,500 |
| 6 4,4'-[9H-Thioxanthen-9,9-diylbis(methylene)]pryidine | 51 | 1,500 |
| 7. 3,3-Bis(4-pyridinylmethyl)-1-phenylindolin-2-one | 56 | 1,500 |
| 8. 4-[2-Methyl-9-(4-pyridinylmethyl)-9H-fluoren-9-ylmethyl]pyridine | 62 | 170 |
| 9. 9,9-Bis(4-pyridinylmethyl)-9H-fluorene | 62 | 340 |
| 10. α-(4-Methoxyphenyl)-α-(4-pyridinylmethyl)-4-pyridinepropane nitrile | 119 | 1,600 |
| 11. 4-[1,2-Dihydro-2-methylene-1-(4-pyridinylmethyl)-1-acenaphthylen-1-yl-methyl]]-pyridine | 120 | 3,300 |
| 12. 5,5-Bis(4-pyridinyl-methyl)-5H-cyclopenta(2,1-B:3,4-B')-dipyridine | 168 | 1,400 |
| 13. 1,3-Dihydro-1-phenyl-3-(4-pyridinylmethyl)-3(4-pyrimidinylmethyl)-2H-indol-2-one | 179 | 1,500 |
| 14. 3,3-Bis(4-pyridinylmethyl)-1,3-dihydro-6-methyl-1-phenyl-2H-indol-2-one | 198 | 4,800 |
| 15. 1,1-Bis(4-pyridinylmethyl)5,6-dihydro-4H-pyrollo(3,2,1-IJ)quinolin-2(1H)-one | 558 | 14,000 |
| 16. 3,3-Bis(4-pyrimidinylmethyl)-1-phenyl-1H-indol-2(3H)-one | 570 | 3,500 |
| 17. 1,3-Dihydro-1-phenyl-3-(1H-pyrazol-4-ylmethyl)-3-(4-pyridinylmethyl)-2H-indol-2-one | 670 | 3,000 |
| 18. 1,3-Dihydro-1-phenyl-3-(4-pyridinylmethyl)-3-(tetrahydro-2-furanylmethyl)-2H-indol-2-one | 1,040 | 34,000 |
| 19. 3,3-Bis(4-pyridinylmethyl)-1,3-dihydro-1-(phenylmethyl)-2H-indol-2-one | 1,168 | 4,500 |

TABLE II-continued

| Compounds | Binding IC$_{50}$ (nM) | ACh Release EC$_{100}$ (nM) |
|---|---|---|
| 20. 3,3-Bis(2-pyrazinylmethyl)-1-phenyl-1H-indol-2(3H)-one | 4,200 | 11,000 |
| 21. 1,3-Dihydro-1-phenyl-3-(3-pyridinylmethyl)--2H-indol-2-one | 6,030 | 12,000 |
| 22. 1,3-Dihydro-1-methyl-3-3-bis(4-pyridinylmethyl)-2-H-indol-2-one | 15,900 | 17,000 |
| 23. 3,3-Bis(3-pyridinylmethyl)-1-phenyl-1H-indol-2(3H)one N-oxide | 50,000 | 100,000 |
| 24. 3,3-Bis(5-pyrimidinyl)-1,3-dihydro-1-phenyl-2H-indol-2-one | 75,900 | 980,000 |
| 25 3,3-Bis(1-methyl-4-piperidinylmethyl)-1,3-dihydro-1-phenyl-2H-indol-2-one | 970,000 | 1,200,000 |
| 26. 3[Bis(2-pyridinyl)-(hydroxy)methyl]-1,3-dihydro-1-phenyl-2H-indol-2-one | 980,000 | 1,000,000 |
| 27. 3,3-Bis[1-(phenylmethyl)-1H-pyrazol-4-ylmethyl]-1,3 dihydro-1-phenyl-2H-indol-2-one | 990,000 | 1,300,000 |
| 28. 3,3-Bis(4-pyridazinyl-methyl)-1,3-dihydro-1-phenyl-2H-indol-2-one | 1,000,000 | 1,000,000 |
| 29. 2-[9-(2-pyridinylmethyl)-9H-fluoren-9-ylmethyl]-pyridine | 1.100.000 | 990,000 |
| 30. 3,3-Bis(2-methyl-4-thiazolylmethyl)-1,3-dihydro-1-phenyl-2H-indol-2-one | 1.200.000 | 980,000 |

EXAMPLE 5

Production of Monoclonal Antibodies Capable of Binding the Binding Protein

Adult female Balb/c mice are primed intraperitoneally with 0.25–1 mg protein of the brain membranes or 0.1–0.25 mg of the substantially purified protein in aluminum potassium sulfate (alum). Two or three booster injections are given at 21 day intervals. Fusions were performed three days after the last boost.

Part B: Fusion

The spleen is removed aseptically and a single cell suspension prepared. The cells are then fused with P3-X63 Ag8.653 myeloma cells at a ratio of 2:1 using 1 ml of polyethylene glycol 1500. The fused cells are washed in serumfree medium, suspended in medium containing HAT and 10 units/ml of insulin, and plated into 96-well microliter plates. Cultures are fed 1 week later with HT medium. When hybrids are detected (approximately 2 weeks after fusion), the supernatants are collected for screening.

Part C: Screening

Culture supernatants are screened for anti-DuP 996 binding protein antibody by an ELISA. 96-well plates are coated with 50 μg of substantially purified DuP 996 binding protein in phosphate buffered saline solution (PBS) for 12 hours at 4° C. Wells are washed with PBS, filled with a 2% solution of bovine serum albumin in PBS, and stored at 4° C. until used. 100 μL of hybridoma supernatant is added to each well and incubated for 2 hours at 25° C. Wells are washed 3 times with PBS and incubated for 2 hours with 50 μL of sheep anti-mouse β-galactosidase linked F(ab')$_2$. After the incubation period and 3 washes with PBS, 50 μL of ortho-Nitrophenyl-β-D-galactosidase (1 mg/ml in PBS containing 100 nM 2-mercaptoethanol) is added to each well. After color development, the absorbance is determined on a microELISA reader at 405 nM.

Those hybridomas displaying substantial activity in the ELISA (greater than three times the value observed with supernatant from P3 myeloma cells) are tested in a radioreceptor binding assay to identify cell lines producing high affinity monoclonal antibodies which interfere with DuP 996 binding to the DuP 996 binding protein. Hybridoma supernatants are incubated with brain membranes for 2 hours at 25° C. 10 nM of [$^3$H]DuP 996 is added and incubated for 1 hour at 25° C. The samples are filtered rapidly under negative pressure on glass fiber filters presoaked in 0.2% polyethylenimine and washed 3 times with ice-cold 50 mM Tris buffer, pH 7.4. Nonspecific binding is determined in the presence of 10 μM DuP 996. Radioactivity is determined by counting in a liquid scintillation counter. The hybridoma supernatants containing the antibody for the DuP 996 binding protein that inhibits the specific binding of [$^3$H]DuP 996 are thereby identified.

Part D: Cloning by Limiting Dilution

The hybrid cell line of interest are cloned at limiting dilution using strict Poison statistics. In this case, approximately one-third of the wells should show growth and the probability is very high that cells growing in a given well are the progeny of a single hybridoma cell.

When sufficient numbers of cells are present in the well, the supernatants are again tested for the presence of monoclonal antibody.

EXAMPLE 6

Part A: The use of Monoclonal Antibodies in Screening Method of Invention

Labeled monoclonal antibodies for the DuP 996 binding protein are incubated with brain membranes (1–2 mg protein) in 50 mM Tris buffer pH 7.4 in the presence or absence of test compounds at 25° C. for 2 hours. The label is selected from the group consisting of radioactive isotopes, enzymes, fluorogenic, chemiluminescent and electrochemical materials. Test compounds are added 10 minutes the monoclonal antibodies. At the end of the 2 hour incubation, the samples are filtered on Whatman GF/B glass filters and washed 3 times with ice-cold buffer. The amount of antibodies bound to the membranes is detected by scintillation counting, spectroscopy, or electrochemical detector. The control represents the specific binding of the labeled monoclonal antibody binding to the DuP 996 binding protein. The nonspecific binding is defined as the amount of labeled of antibodies retained on the membranes and the filter that is not displaced by 10 μM DuP 996. Chemicals that can displace the binding of the antibody to the DuP 996 binding protein should be active in binding to the same protein.

EXAMPLE 7

Part A: Effect of pH on Binding

Brain membranes (1–2 mg protein) were incubated with 10 nM tritiated DuP 996 in 100 mM Tris buffer at different pH of either 5, 6, 7, 8, 9 or 10 for 60 minutes in room temperature. The samples were filtered and washed according to the method described in Example 1, Part B. Nonspecific binding was determined in the presence of 10 μM DuP 996.

EXAMPLE 8

Part A: Effect of Temperature on Binding

Brain membranes (1-2 mg protein) were incubated with 10 nM tritiated DuP 996 in 50 mM Tris-HCl buffer, pH 7.4, for 60 minutes at different temperatures of either 4°, 12°, 25°, or 37° C. The samples were filtered and washed according to the method described in Example 1, Part B. Nonspecific binding was determined in the presence of 10 μM DuP 996.

What is claimed is:

1. A screening method to evaluate a compound for enhancing endogenous stimulus-induced neurotransmitter release, said neurotransmitter being selected from the group consisting of acetylcholine, dopamine, or serotonin, the method comprising:
   (a) incubating unlabeled compound with radiolabeled 3,3-bis(4-pyridinylmethyl)-1-phenylindolin-2-one, and a substantially purified protein extracted from brain membranes which enhances the release of said neurotransmitters, the protein having a binding affinity constant of at least 2.9±0.8 nM for tritiated 3,3-bis(4-pyridinylmethyl)-1-phenylindolin-2-one as determined by a Scatchard analysis and said protein being trypsin sensitive and phospholipase C insensitive; and
   (b) determining the extent to which the unlabeled compound inhibits the binding of the radiolabeled compound with the protein.

2. A method according to claim 1 wherein the radiolabel is selected from the group consisting of tritium, carbon-14, phosphorus-32, Iodide-125, Iodide-131 and Technetium-99M.

3. A method according to claim 1 wherein the radiolabel is tritium.

* * * * *